(12) United States Patent
Bornemann (10) Patent No.: US 8,966,695 B1
(45) Date of Patent: Mar. 3, 2015

(54) CLOSED MOUTH TOOTHBRUSH

(76) Inventor: Nancy Bornemann, Hazen, ND (US)

( * ) Notice: Subject to any disclaimer, the term of this patent is extended or adjusted under 35 U.S.C. 154(b) by 0 days.

(21) Appl. No.: 13/434,601

(22) Filed: Mar. 29, 2012

Related U.S. Application Data

(60) Provisional application No. 61/484,405, filed on May 10, 2011.

(51) Int. Cl.
*A61C 17/34* (2006.01)
*A46B 9/04* (2006.01)

(52) U.S. Cl.
CPC .................................. *A46B 9/045* (2013.01)
USPC ................................. 15/22.1; 15/22.2; 15/23

(58) Field of Classification Search
USPC ................. 15/22.2, 23, 167.1, 22.1
See application file for complete search history.

(56) References Cited

U.S. PATENT DOCUMENTS

| | | | | |
|---|---|---|---|---|
| 1,795,098 A | * | 3/1931 | Scadding | 15/23 |
| 2,179,402 A | * | 11/1939 | Doran | 15/22.1 |
| 2,314,117 A | * | 3/1943 | Beckner | 15/23 |
| 3,160,902 A | * | 12/1964 | Aymar | 15/22.1 |
| 3,451,086 A | * | 6/1969 | Burgett | 15/23 |
| 4,538,315 A | * | 9/1985 | Barth | 15/23 |
| 4,603,448 A | * | 8/1986 | Middleton et al. | 15/22.1 |
| 4,845,796 A | * | 7/1989 | Mosley | 15/23 |
| 5,177,827 A | * | 1/1993 | Ellison | 15/22.1 |
| 5,699,575 A | * | 12/1997 | Peifer | 15/23 |
| 6,582,224 B1 | * | 6/2003 | Lilien et al. | 433/1 |
| 7,543,348 B2 | * | 6/2009 | Le | 15/65 |
| 2008/0216257 A1 | * | 9/2008 | Ahadpour et al. | 15/22.1 |
| 2009/0276972 A1 | * | 11/2009 | Dugan | 15/167.2 |

* cited by examiner

*Primary Examiner* — Randall Chin
(74) *Attorney, Agent, or Firm* — Michael I. Kroll (57) ABSTRACT

A first embodiment of the present invention is a closed mouth toothbrush which comprises a flexible brush head. A shaft is connected at a first end to the flexible brush head. An ergonomic handle is connected to a second end of the shaft, whereby a person can grip the ergonomic handle comfortably and manually move the shaft in a reciprocating manner to cause the flexible brush head to clean all surfaces within a closed mouth of the person. A second embodiment of the present invention contains a mechanism for automatically moving the shaft in a reciprocating manner from within the ergonomic handle to cause the flexible brush head to clean all surfaces within a closed mouth of the person.

8 Claims, 10 Drawing Sheets

CLOSED MOUTH TOOTHBRUSH

RELATED APPLICATIONS

This application is subject to U.S. provisional application Ser. No. 61/484,405 filed 10 May 2011.

Please incorporate by reference all information in said provisional applications into this instant invention.

BACKGROUND OF THE INVENTION

1. Field of the Invention

The present invention relates generally to toothbrushes and, more specifically, to a closed mouth toothbrush comprising a curvilinearly shaped flexible brush head forming seat for a plurality of circumferentially extending bristles manufactured of a material selected from fibers and polymerics, extending radially, with the bristle's periphery enveloping a curvilinear elliptical shape to provide a way for performing a cleaning task of all the interior oral cavity surfaces.

The cleaning task comprises moving the flexible brush head in a reciprocating motion for brushing the interior cheek wall, teeth, gums, roof of mouth and tongue with the mouth closed, thereby all germs are retained within the mouth until the oral cavity is rinsed. In conjunction with a manual embodiment of the present invention, the present invention further envisions an electric embodiment in which the flexible brush head is fixed to a motorized shaft that is selectively actuatable reciprocatively.

2. Description of the Prior Art

There are other toothbrushes designed for reciprocating movement during use.

While these toothbrushes may be suitable for the purposes for which they where designed, they would not be as suitable for the purposes of the present invention as heretofore described.

It is thus desirable to provide a closed mouth toothbrush having a flexible brush head that conforms to a surface being cleaned.

It is further desirable to provide a closed mouth toothbrush having a flexible brush head being in a curvilinear elliptical shape with a distal end having a smaller cross sectional area than a middle portion to aid in cleaning between superjacent skin folds.

SUMMARY OF THE PRESENT INVENTION

Most if not all toothbrushes now splatter toothpaste and germs all over the bathroom mirror and sink especially by children. The reason is because the person using them has to open their mouth up so wide to get to the back teeth and all the while having to switch hands or direction to get all the places in the mouth. With the closed mouth toothbrush there is no splatter, no germs flying everywhere, all the germs stay within the mouth until it's rinsed and not all over the bathroom.

Germs and bacteria thrive inside the human mouth. Issues that can arise include gum disease, gingivitis, halitosis, tooth decay, and more. People are busy and always on the go and may neglect their teeth. Children often rush through the brushing process and may not obtain a thorough cleaning. Even an adult may not do an effective job of cleaning their teeth, gums, mouth, and tongue. It is difficult to achieve a thorough cleaning using the toothbrushes currently on the market. A more efficient option is needed.

The closed mouth toothbrush is capable of cleaning the entire mouth and teeth. The present invention provides the toothbrush having a flexible brush head that is incorporated into either a manual or motor driven reciprocatable toothbrush in which the flexible brush head is able to clean not only the teeth, but also the gums, the roof of the mouth, the side of the mouth, and all sides of the tongue. The flexible brush head cleans the mouth quickly and thoroughly, while consumers will appreciate the cleanliness and convenience that the present invention affords.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

A primary object of the present invention is to provide a closed mouth toothbrush, so that all the germs stay inside the mouth until the person rinses.

Another object of the present invention is to provide a closed mouth toothbrush having a flexible brush head that will engage all surfaces within an oral cavity during a cleaning session.

Yet another object of the present invention is to provide a closed mouth toothbrush having a flexible brush head that extends curvilinearly from a handle.

Still yet another object of the present invention is to provide a closed mouth toothbrush, in which the flexible brush head includes a plurality of radially extending bristles.

An additional object of the present invention is to provide a closed mouth toothbrush, in which the flexible brush head includes the bristles manufactured of a material selected from fibers and polymerics.

A further object of the present invention is to provide a closed mouth toothbrush, in which the flexible brush head includes the bristles forming an envelope of a curvilinear elliptical shape for performing a cleaning task within the interior oral cavity fold surfaces.

A yet further object of the present invention is to provide a closed mouth toothbrush incorporating a handle fixedly attached via a shaft to the flexible brush head.

A still yet further object of the present invention is to provide a closed mouth toothbrush having a flexible brush head that is manually moved in a reciprocating fashion while the mouth is closed during a cleaning session.

Another object of the present invention is to provide a closed mouth toothbrush wherein the handle houses a motor.

Yet another object of the present invention is to provide a closed mouth toothbrush, wherein the handle further incorporates a mechanism for converting rotational motion of the motor into a reciprocating motion.

Still yet another object of the present invention is to provide a closed mouth toothbrush, in which the handle contains a rechargeable battery to energize the motor.

An additional object of the present invention is to provide a closed mouth toothbrush, in which the handle further comprises a switch for selectively engaging and disengaging the motor.

A further object of the present invention is to provide a closed mouth toothbrush that can clean all surfaces within the human oral cavity not just the teeth.

A yet further object of the present invention is to provide a closed mouth toothbrush having a flexible brush head for cleaning the whole mouth, gums, inside the cheeks, roof of the mouth and the tongue in less time than it takes for any other manual or electric toothbrush which just cleans the teeth.

A still yet further object of the present invention is to provide a closed mouth toothbrush having a flexible brush head that can wrap around the back molars and contours of the mouth.

Additional objects of the present invention will appear as the description proceeds.

The present invention overcomes the shortcomings of the prior art by providing a closed mouth toothbrush comprising a curvilinearly shaped flexible brush head forming a seat for a plurality of circumferentially extending bristles manufactured of a material selected from fibers and polymerics, extending radially, enveloping a curvilinear elliptical shape to provide a way for performing a cleaning task of all the interior oral cavity surfaces.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the Figures illustrate the closed mouth toothbrush of the present invention. With regard to the reference numerals used, the following numbering is used throughout the various drawing figures.

First Embodiment 10 closed mouth toothbrush
12 flexible brush head of toothbrush 10
14 shaft of toothbrush 10
16 first end of shaft 14
18 ergonomic handle of toothbrush 10
20 second end of shaft 14
22 person
24 closed mouth of person 22
26 shank of flexible brush head 12
28 bristles of flexible brush head 12

Second Embodiment 30 closed mouth toothbrush
32 flexible brush head of toothbrush 30
34 shaft of toothbrush 30
36 first end of shaft 34
38 ergonomic handle of toothbrush 30
40 second end of shaft 34
42 person
44 automatically moving mechanism of toothbrush 30
46 closed mouth of person 42
48 shank of flexible brush head 32
50 bristles of flexible brush head 32
52 motor of mechanism 44
54 power source of mechanism 44
56 battery for power source 54
58 on/off switch of mechanism 44
60 multi-speed adjuster of mechanism 44
62 end cap on ergonomic handle 38
64 O-ring between ergonomic handle 38 and end cap 62
66 rechargeable battery for power source 54

DETAILED DESCRIPTION OF THE PREFERRED EMBODIMENT

The following discussion describes in detail two embodiments of the present invention. This discussion should not be construed, however, as limiting the invention to those particular embodiments, practitioners skilled in the art will recognize numerous other embodiments as well. For definition of the complete scope of the invention, the reader is directed to appended claims.

Figure 1:
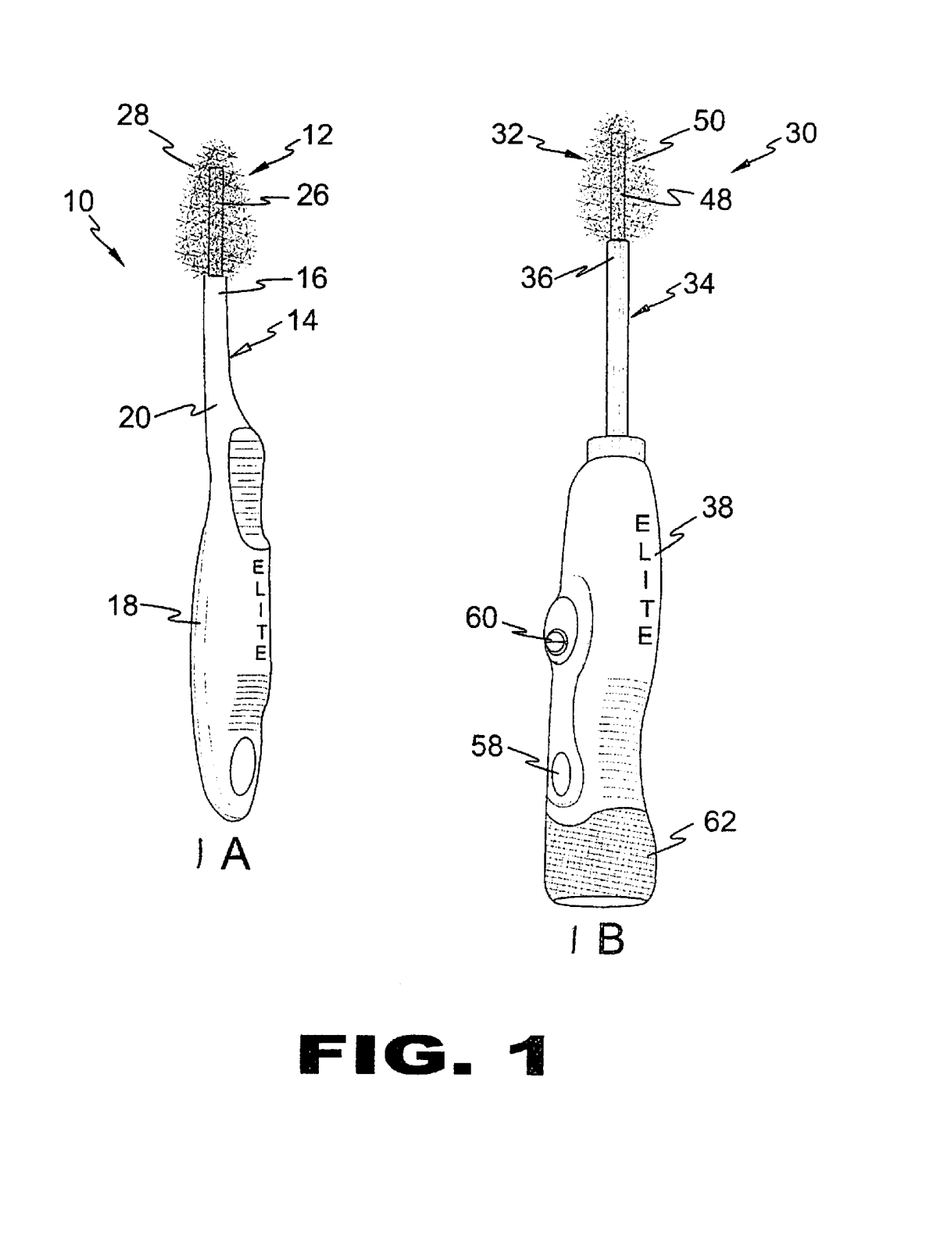
FIGS. 1A and 1B are an illustrative perspective view of two embodiments of the present invention, wherein the first embodiment is a manual toothbrush while the second embodiment is an electric toothbrush.
Figure 2:
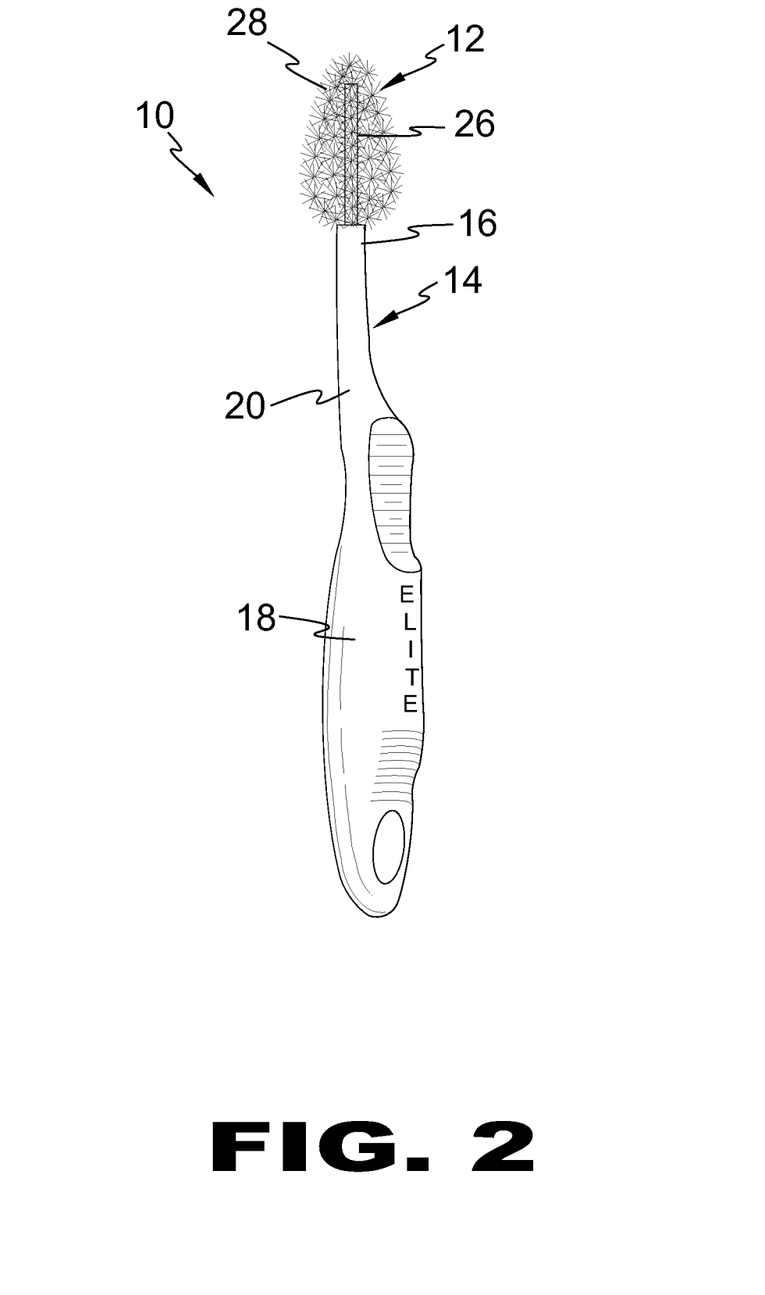
FIG. 2 is a perspective view of the first embodiment of the present invention.
Figure 3:
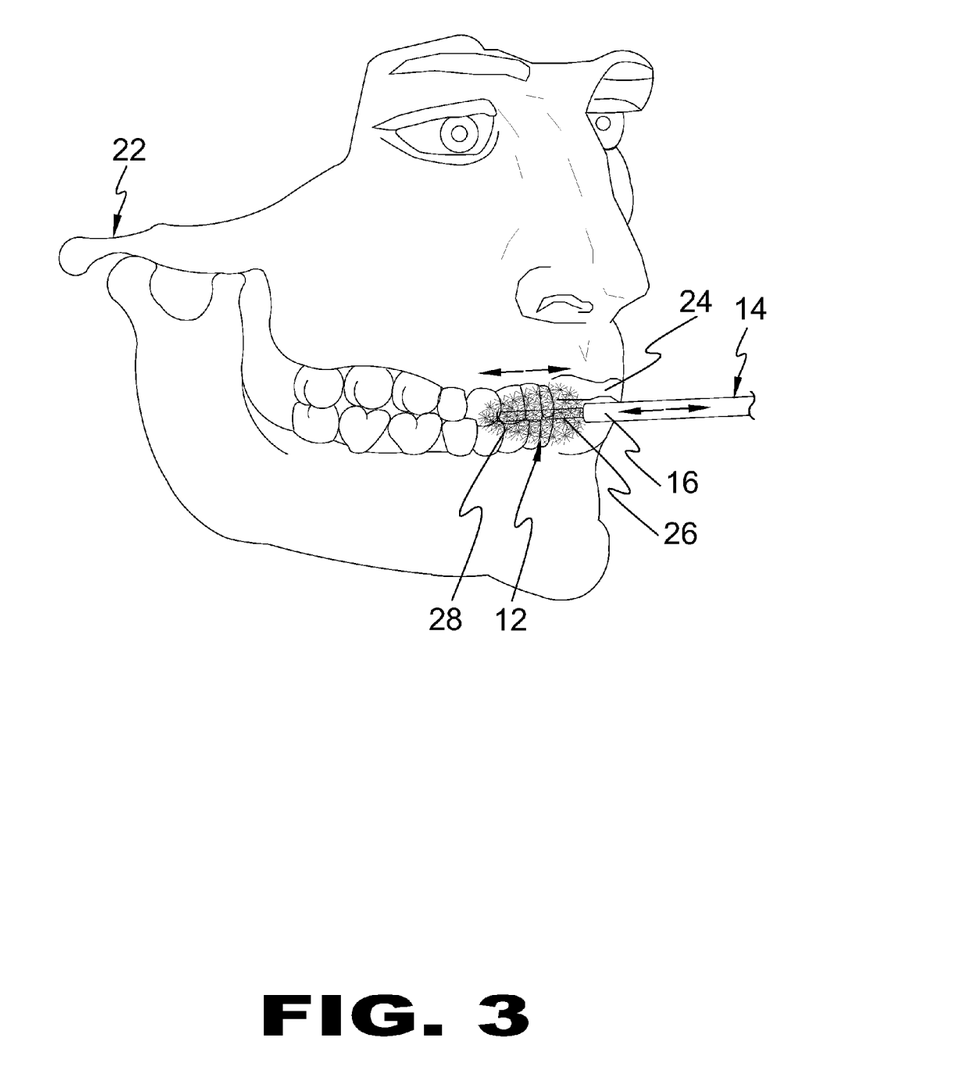
FIG. 3 is perspective view of a portion of the first embodiment of the present invention cleaning the teeth.
Figure 4:
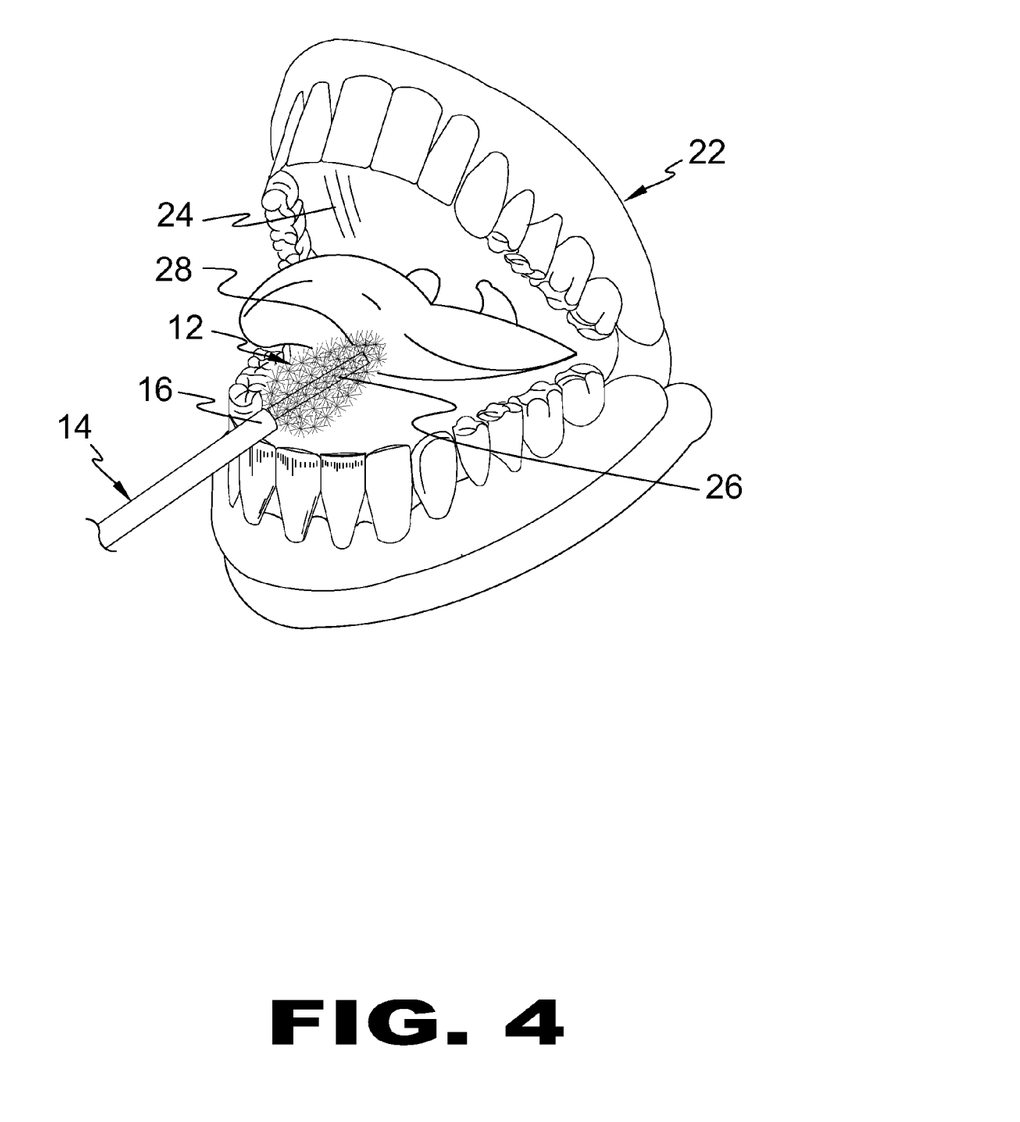
FIG. 4 is a perspective view of a portion of the first embodiment of the present invention cleaning the mouth and under the tongue.

A first embodiment of the present invention, as shown in FIGS. 1A and 2 is a closed mouth toothbrush 10 which comprises a flexible brush head 12. A shaft 14 is connected at a first end 16 to the flexible brush head 12. An ergonomic handle 18 is connected to a second end 20 of the shaft 14. As shown in FIGS. 3 and 4, a person 22 can grip the ergonomic handle 18 comfortably and manually move the shaft 14 in a reciprocating manner to cause the flexible brush head 12 to clean all surfaces within a closed mouth 24 of the person 18, such as the teeth, mouth and under the tongue.

The flexible brush head 12 consists of a shank 26 extending from the first end 16 of the shaft 14. The flexible brush head 12 further contains a plurality of bristles 28. The plurality of bristles 28 radially extend about the shank 26. The plurality of bristles 28 can be comprised from fibers or from polymerics.

Figure 5:
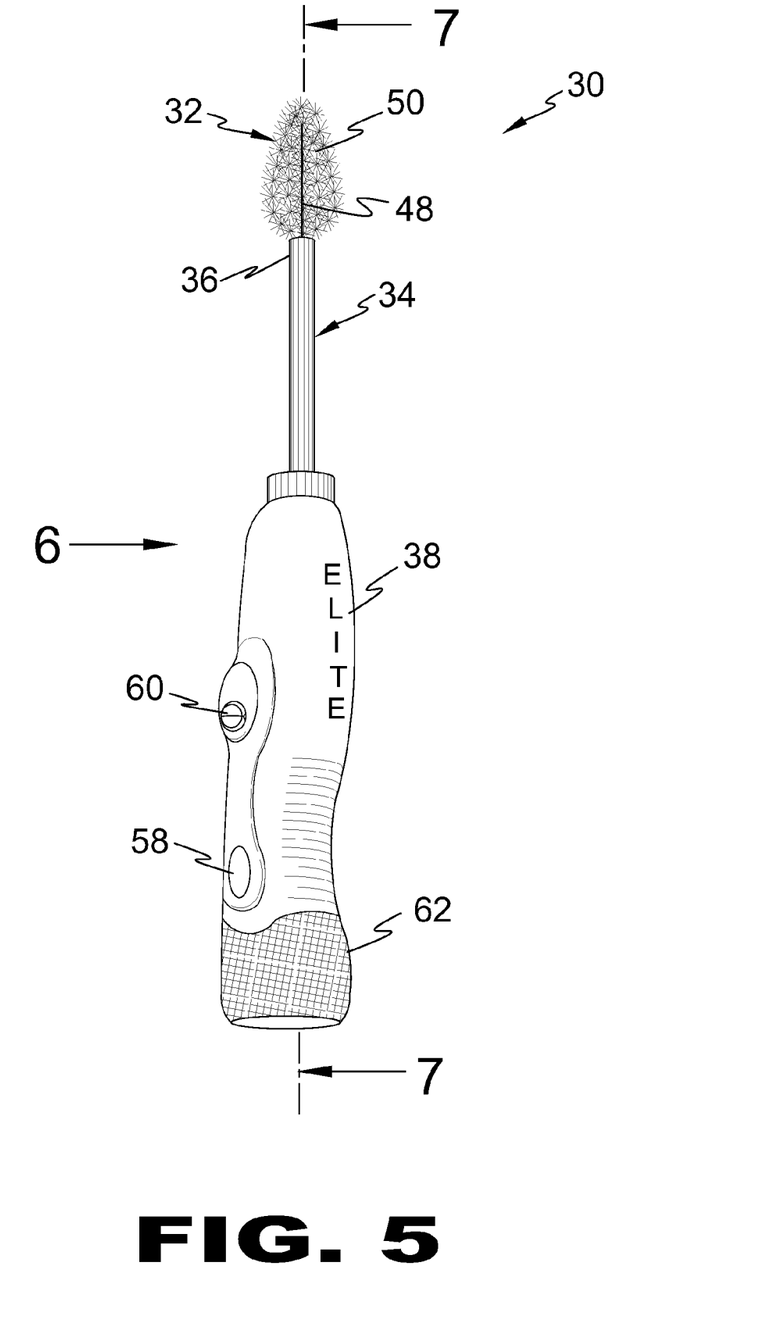
FIG. 5 is a perspective view of the second embodiment of the present invention.
Figure 6:
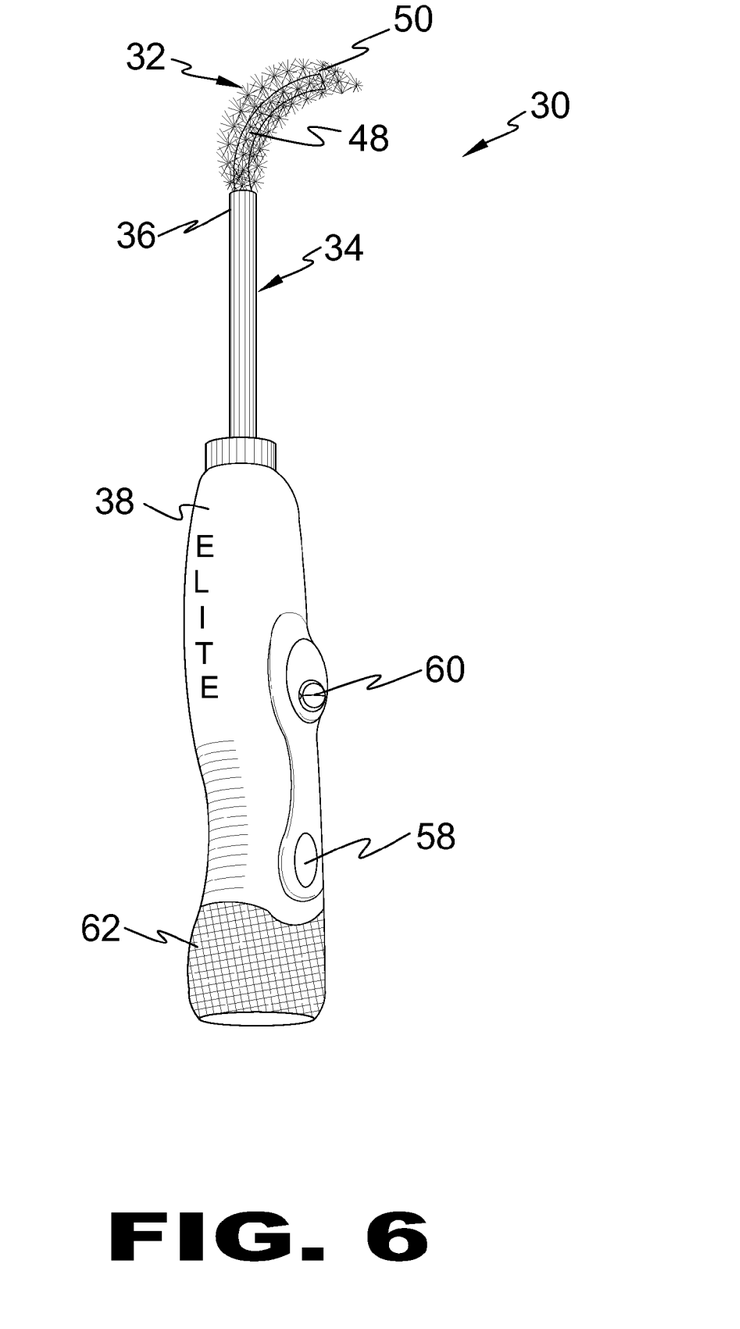
FIG. 6 is a perspective view of the second embodiment of the present invention taken in the direction of arrow 6 in FIG. 5.
Figure 7:
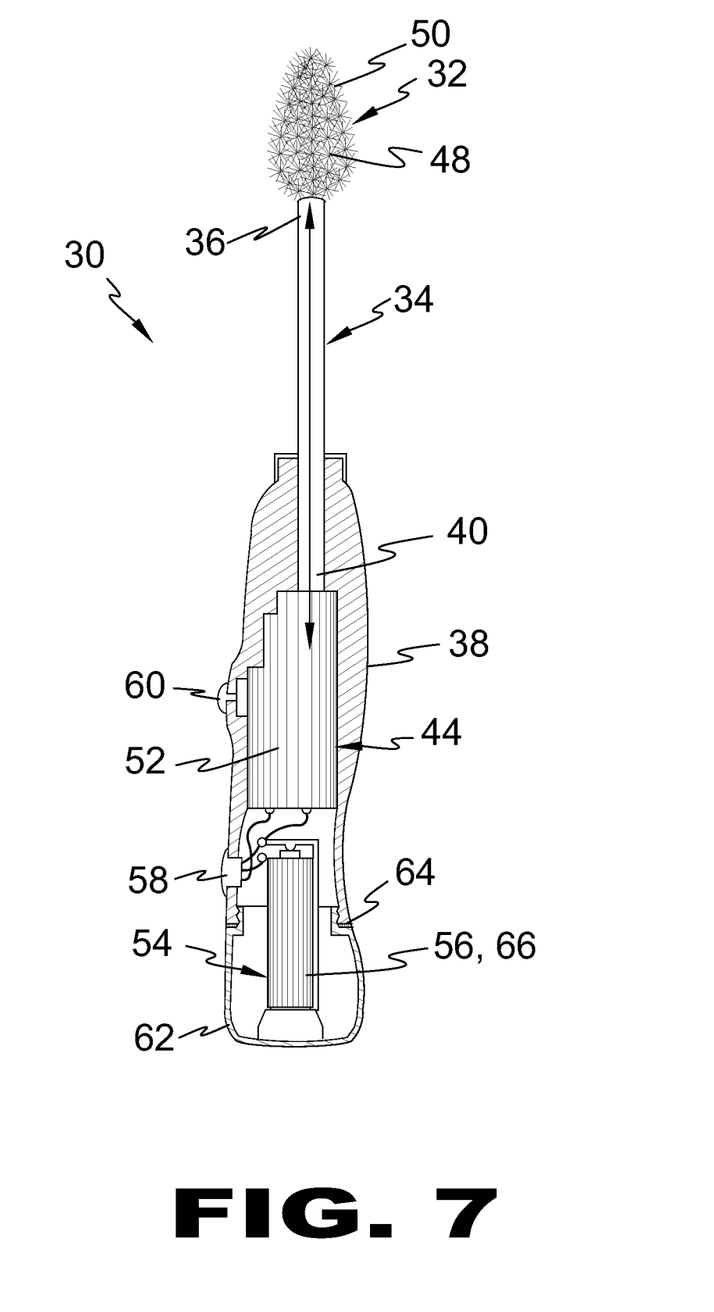
FIG. 7 is a cross sectional view of the second embodiment of the present invention taken along line 7-7 in FIG. 5.
Figure 8:
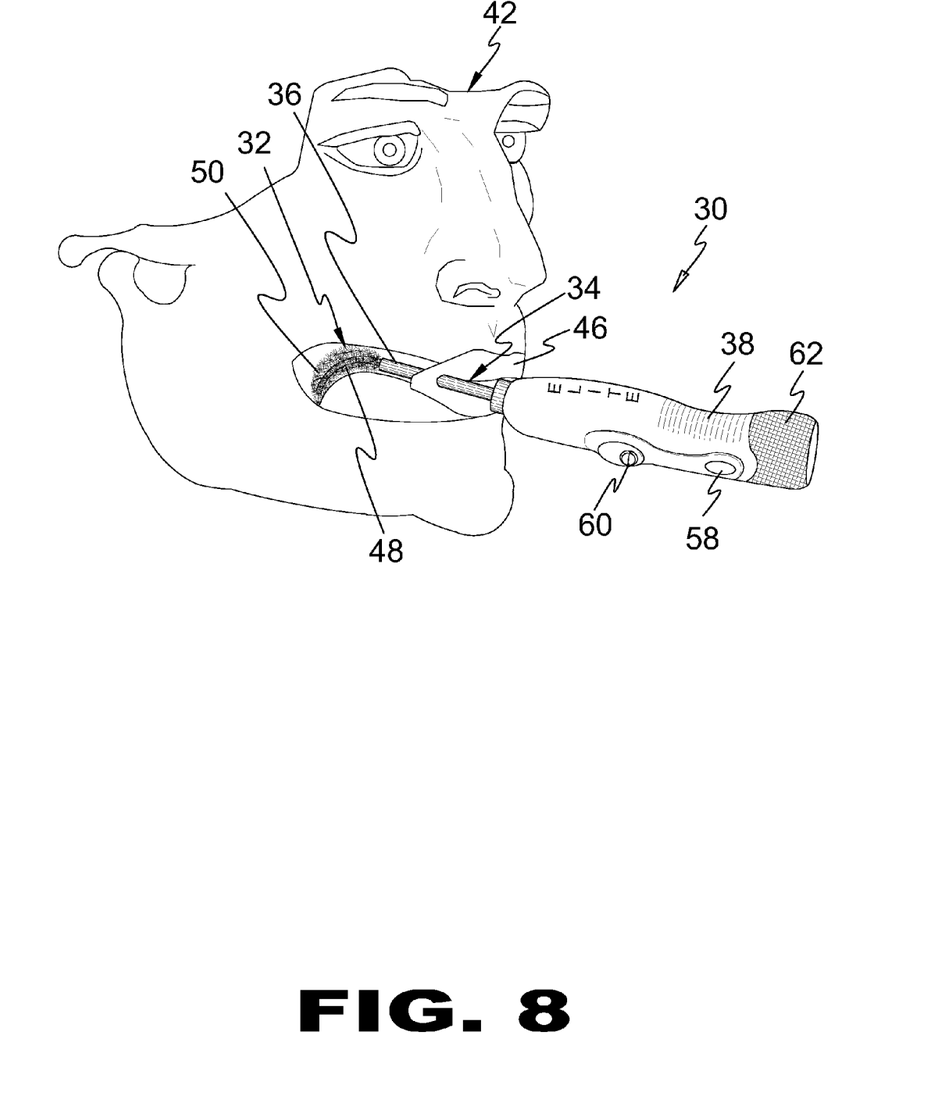
FIG. 8 is a perspective view of the second embodiment of the present invention cleaning the roof of the mouth and top of the tongue.
Figure 9:
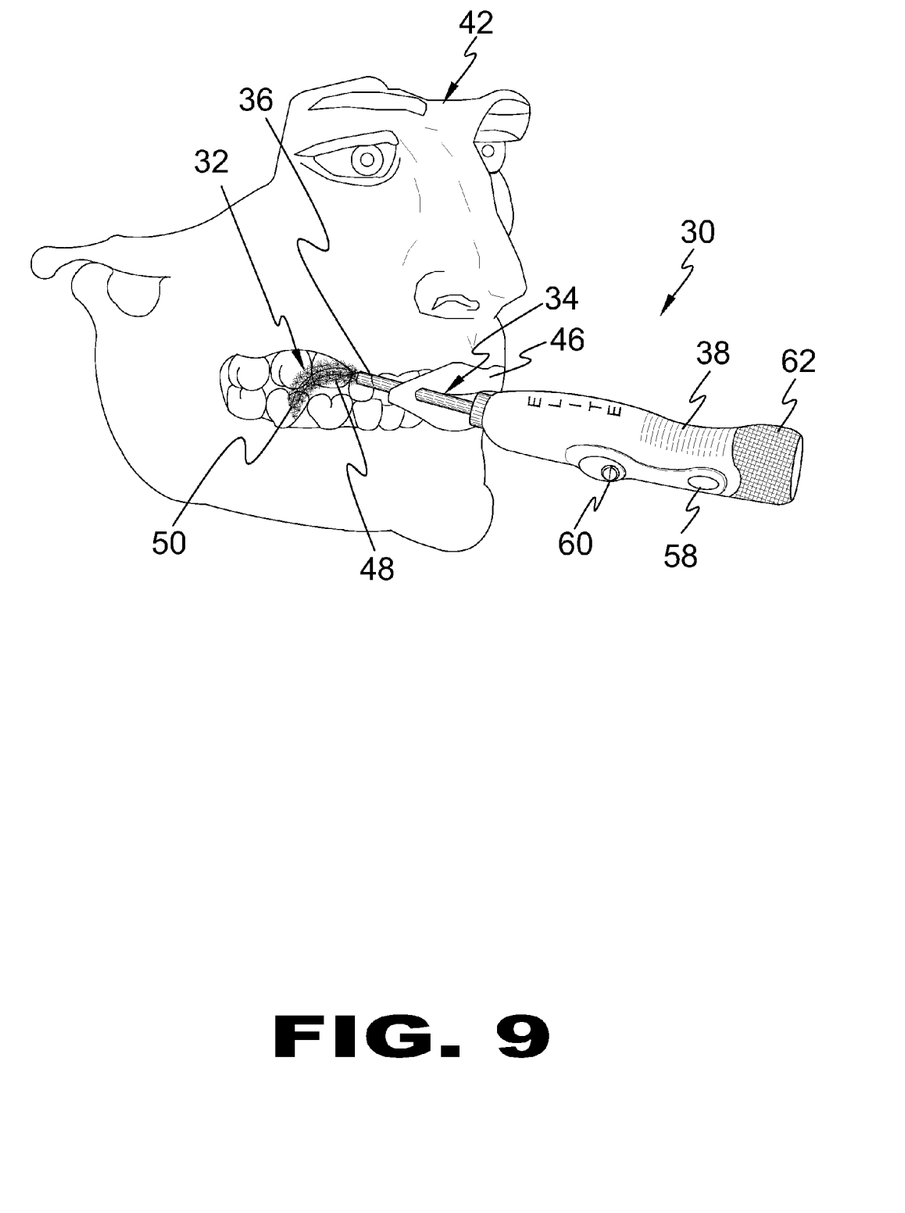
FIG. 9 is a perspective view of the second embodiment of the present invention cleaning the top and bottom teeth at the same time.
Figure 10:
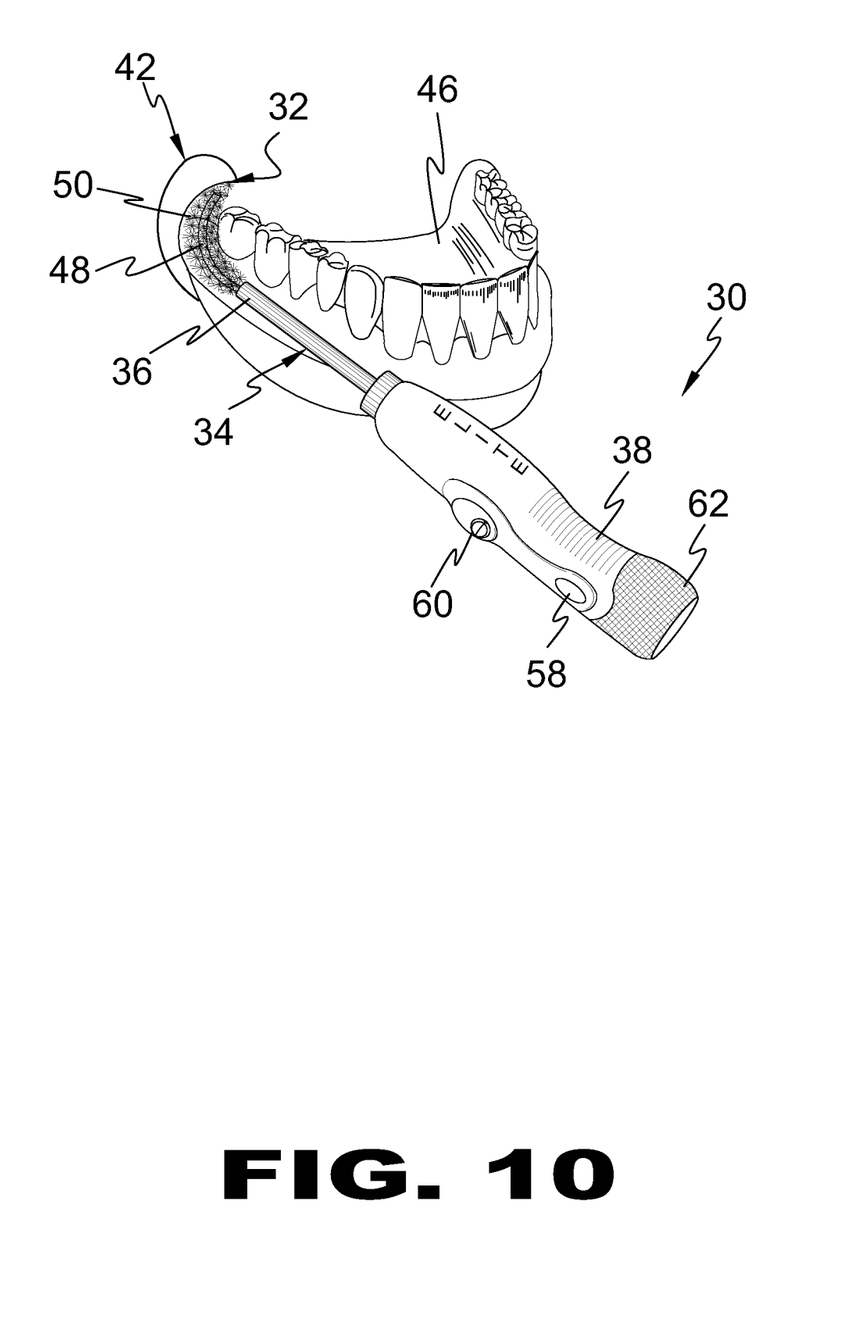
FIG. 10 is a perspective view of the second embodiment of the present invention cleaning around the back of the teeth and inside the cheek.

A second embodiment of the present invention, as shown in FIGS. 1B, 5 and 6 is a closed mouth toothbrush 30 which comprises a flexible brush head 32. A shaft 34 is connected at a first end 36 to the flexible brush head 32. An ergonomic handle 38 contains a second end 40 of the shaft 34 therein, whereby a person 42 can grip the ergonomic handle 38 comfortably. A mechanism 44, as best shown in FIG. 7 is for automatically moving the shaft 34 in a reciprocating manner from within the ergonomic handle 38 to cause the flexible brush head 32 to clean all surfaces within a closed mouth 46 of the person 42, such as the roof of the mouth, top of the tongue, top and bottom teeth at the same time, around the back of the teeth and inside the cheek, as shown in FIGS. 8, 9 and 10.

The flexible brush head 32 consists of a shank 48 having a curvilinearly shape, whereby the shank 48 extends from the first end 36 of the shaft 34. The flexible brush head 32 further contains a plurality of bristles 50. The plurality of bristles 50 radially extend about the shank 48. The plurality of bristles 50 form an envelope of a curvilinear elliptical shape. The plurality of bristles 50 can be comprised from fibers or from polymerics.

The automatically moving mechanism 44 comprises a motor 52 carried within the ergonomic handle 38. A power source 54 is electrically connected to the motor 52. The shaft 34 is adjustably coupled into the motor 52, whereby the motor 52 will cause the shaft 34 to move in the reciprocating manner. The power source 54 is comprised of a battery 56 in the ergonomic handle 38. An on/off switch 58 on the ergonomic handle 38 is electrically connected between the motor 52 and the battery 56. A multi-speed adjuster 60 on the ergonomic handle 38 is in engagement with the motor 52.

An end cap 62 is on the ergonomic handle 38 to gain access to the battery 56. An O-ring 64 is between the end cap 62 and the ergonomic handle 38, whereby when the end cap 62 is threaded on the ergonomic handle 38, the O-ring 64 will provide a watertight seal. The power source 54 can also be a rechargeable battery 66.

The invention claimed is:

1. A closed mouth toothbrush which comprises;
    a) a flexible brush head comprising a shank with bristles radially extending about said shank and said bristles forming an envelope of a curvilinear elliptical shape;
    b) a shaft connected at a first end to said shank of the flexible brush head, said shaft being adapted to enter said closed mouth, and said shank being sufficiently flexible to conform to areas necessary for brushing an interior cheek wall, teeth gums, roof of mouth and tongue and whereby all germs are retained within the mouth until the oral cavity of said mouth is rinsed;
    c) an ergonomic handle contains a second end of the shaft therein, whereby a person can grip the ergonomic handle comfortably; and
    d) means for automatically moving the shaft in a reciprocating manner from within the ergonomic handle to cause the flexible brush head to clean all surfaces within a closed mouth of the person.

2. The closed mouth toothbrush as recited in claim 1, wherein said bristles are comprised from fibers.

3. The closed mouth toothbrush as recited in claim 1, wherein said bristles are comprised from polymerics.

4. The closed mouth toothbrush as recited in claim 1, wherein the automatically moving means comprises:
    a) a motor carried within the ergonomic handle;
    b) a power source electrically connected to the motor;
    c) the shaft adjustably coupled into the motor, whereby the motor will cause the shaft to move in the reciprocating manner;
    d) a multi-speed adjuster on said handle connected to said automatically moving means; and
    e) an on/off switch on said handle to connect or disconnect said power source to said motor.

5. The closed mouth toothbrush as recited in claim 4, wherein the power source is comprised of a battery in the ergonomic handle.

6. The closed mouth toothbrush as recited in claim 5, further comprising an end cap on the ergonomic handle to gain access to the battery, and said on/off switch is between said multi-speed adjuster and said end cap.

7. The closed mouth toothbrush as recited in claim 6, further comprising an O-ring between the end cap and the ergonomic handle, whereby when the end cap is threaded on the ergonomic handle, the O-ring will provide a watertight seal.

8. The closed mouth toothbrush as recited in claim 5, wherein the power source is a rechargeable battery.

* * * * *